US007274683B2

(12) United States Patent
Segal

(10) Patent No.: US 7,274,683 B2
(45) Date of Patent: Sep. 25, 2007

(54) METHOD AND APPARATUS FOR A TELECOMMUNICATIONS NETWORK TO COMMUNICATE USING AN INTERNET PROTOCOL

(75) Inventor: Niranjan Nath Segal, Arlington, TX (US)

(73) Assignee: Motorola, Inc., Schaumburg, IL (US)

( * ) Notice: Subject to any disclaimer, the term of this patent is extended or adjusted under 35 U.S.C. 154(b) by 939 days.

(21) Appl. No.: 10/160,895

(22) Filed: Jun. 3, 2002

(65) Prior Publication Data
US 2003/0128693 A1 Jul. 10, 2003

(51) Int. Cl.
*H04L 12/66* (2006.01)
(52) U.S. Cl. ...................................................... 370/352
(58) Field of Classification Search ... 370/389–395.31, 370/395.5–395.54, 400–408, 352–365
See application file for complete search history.

(56) References Cited

U.S. PATENT DOCUMENTS

| 6,256,389 | B1 | 7/2001 | Dalrymple et al. |
| 6,292,478 | B1 | 9/2001 | Farris |
| 6,359,880 | B1 | 3/2002 | Curry et al. |
| 6,539,077 | B1 | 3/2003 | Ranalli et al. |
| 6,996,087 | B2* | 2/2006 | Ejzak .......................... 455/560 |
| 2002/0024943 | A1* | 2/2002 | Karaul et al. ................ 370/338 |
| 2003/0007482 | A1* | 1/2003 | Khello et al. ................ 370/352 |
| 2003/0081754 | A1* | 5/2003 | Esparza et al. ......... 379/221.01 |

OTHER PUBLICATIONS

Falstrom, P. "Network Working Group". Cisco Systems Inc., Sep. 2000.

* cited by examiner

*Primary Examiner*—Doris H. To
*Assistant Examiner*—Thai Hoang

(57) ABSTRACT

The present invention reduces network operator memory requirements, administrative overhead, and operational costs by enabling a solution for SS7/IP communication that uses a single domain (e164.arpa) in ENUM for numbering schemes such as E.164, E.212, and E.214. Employing the present invention enables the SUA to deliver SCCP-user messages to the destination node using Global Title Information based on IMSI or E.164 numbers. Network operators populate ENUM databases with MAP URIs associated with mobility services such as MSC, HLR, and VLR. End point service node IP addresses, associated with a set of services, are stored in ENUM corresponding to the SAPC belonging to the local operator for a given PLMN. These end node IP addresses then are returned in the ENUM/DNS response to an E.164-based query.

6 Claims, 5 Drawing Sheets

| SERVICE/PROTOCOLS | SAPC | PLMN 1 DB | PLMN 2 DB | PLMN N DB | COMMENTS |
|---|---|---|---|---|---|
| E.212 | 1-817-822-1999 | X | X | X | MOBILITY SERVICES |
| E.214 | 1-817-822-2000 | | | X | DATA TRANSLATION |
| POINT CODE | 1-817-822-2001 | X | | | SS7 LEGACY NETWORK SUPPORT |
| UFMI | 1-817-822-2002 | | X | | DISPATCH SERVICE |
| MAP BASED SERVICES | 1-817-822-2003 | X | X | X | HLR, VLR, SMS |
| CAP BASED SERVICES | 1-817-822-2004 | X | | | PRE-PAID etc. |
| UNUSED CODES | X-XXX-XXX-XXXX | | | | RESERVED FOR FUTURE SERVICES |
| E.164 | NA | X | X | X | ENUM BASIS |

*FIG.1*

| PLMN | SAPC | AVAILABLE SERVICE/PROTOCOL | | | | |
|---|---|---|---|---|---|---|
| | | SIP | MAP | CAP | DISPATCH | PROTOCOL |
| 1 | 1-817-822-1999 | | X | X | | (SUA), (SS7-SG) |
| 2 | 1-817-707-2001 | | X | | X | (M2UA) |
| 3 | 1-214-797-2001 | X | X | X | | (SIP), (M3UA) |
| 4 | 1-212-363-1988 | | X | | X | (IUA) |
| 5 | 1-212-676-1111 | | X | X | X | (SUA) |
| 6 | 1-516-676-0000 | X | X | X | | (SIP), (SUA) |
| 7 | 1-202-765-0000 | | X | | | (SS7-SG) |
| N | 1-202-676-0000 | X | X | | | (SIP), (SUA) |

*FIG.2*

METHOD AND APPARATUS FOR A TELECOMMUNICATIONS NETWORK TO COMMUNICATE USING AN INTERNET PROTOCOL

FIELD OF THE INVENTION

The present invention relates generally to communication systems and, in particular, to telecommunications networks communicating using an Internet protocol.

BACKGROUND OF THE INVENTION

Today, Signaling System 7 (SS7) includes almost all of the voice-based applications supporting supplementary voice services and mobility/roaming services provided by the wireless operators. Present SS7 signaling is transported exclusively over the SS7/PSTN (Public Switched Telephone Network) using the SS7 transport protocols, namely MTP3/2/1, over T1/E1 lines. There is a vast SS7 installed base in both wire-line and wireless networks. These networks are reliable but relatively expensive and less flexible than Internet protocol (IP)-based networks. Thus, industry is seeking to replace the SS7 transport protocols with IP.

To this end, the SIGTRAN working group of the Internet Engineering Task Force (IETF) has been focused on the transport of packet-based PSTN signaling over IP networks, defining a number of SS7/IP user adaptation protocols including M2UA, M3UA, IUA, and SUA. Two of the key problems encountered when developing SS7/IP user adaptation protocols are discovering the appropriate service application node for messages and efficiently routing and interfacing with the legacy SS7 networks. Certain mobility services such as the registration of a mobile subscriber, for example, pose a special challenge. As in the mobile environment, it is the International Mobile Station Identifier (IMSI), assigned in accordance with the International Telecommunications Union (ITU) E.212 standard, that is used for registering and authenticating a subscriber, rather than an E.164 number. Therefore, in order to provide mobility services and common, E.164-number-associated services (such as a simple phone call, short message service (SMS), etc.), two separate domain name service (DNS)-based database, storage, routing, and administration schemes would presently need to be deployed, one based on E.164 (e.g., using the ENUM service (per the IETF standard RFC 2916)) and another based on E.212/DNS, not to mention other domains that might need to be added depending on the services associated with other global titles (GTs). Moreover, such a solution would be proprietary and would not likely be widely accepted.

Alternatively, the translation of the GT Information to an IP address could be done using common, external services such as those provided by ENUM/DNS servers. However, for ENUM (DNS) to be used for mapping mobile numbers to IP addresses we need to define a unique domain for each numbering plan (e.g, e164.arpa, e212.arpa, and e214.arpa). In addition to creating new domains by the Internet Assigned Numbers Authority (IANA), there is tremendous work that would need to be done to develop the procedures to administer a massive database of all of the E.164/212/214 numbers. Each of these numbers would need to be mapped to the IP address corresponding to the appropriate SS7 node in the appropriate operator's system (operators may have multiple SUA nodes as they scale their systems). Thus, a common solution based on ENUM/DNS, e.g., that does not require the administration of all of the E.164/212/214 numbers to provide service discovery and service node identification (i.e., retrieval of the destination IP address) would be preferred over those presently proposed. Therefore, a need exists for an apparatus and method enabling such a solution for SS7/IP communication.

BRIEF DESCRIPTION OF THE DRAWINGS

FIG. 1 is a table showing an example of PLMNs providing a set of services/protocols, each service/protocol represented by a unique SAPC.

FIG. 2 is a table showing an example of PLMNs providing a set of services/protocols, each PLMN represented by a unique SAPC.

DESCRIPTION OF A PREFERRED EMBODIMENT

The present invention reduces network operator memory requirements, administrative overhead, and operational costs by enabling a solution for SS7/IP communication that uses a single domain (e164.arpa) in ENUM for numbering schemes such as E.164, E.212, and E.214. Employing the present invention enables the SUA to deliver SCCP-user messages to the destination node using Global Title Information based on IMSI or E.164 numbers. Network operators populate ENUM databases with MAP URIs associated with mobility services such as MSC, HLR, and VLR. End point service node IP addresses, associated with a set of services, are stored in ENUM corresponding to the SAPC belonging to the local operator for a given PLMN. These end node IP addresses then are returned in the ENUM/DNS response to an E.164-based query.

Figure 3:
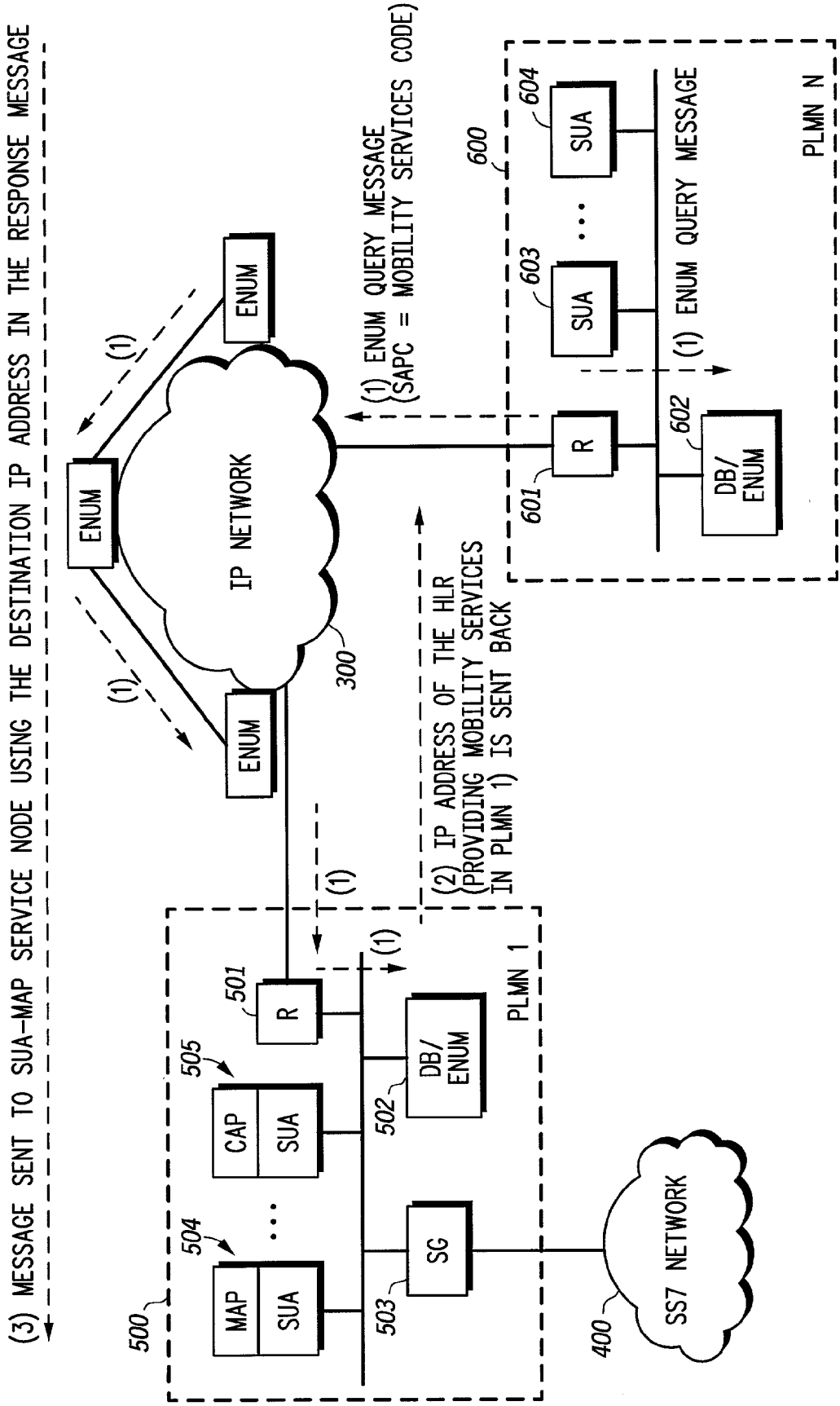
FIG. 3 is a block diagram depiction of PLMNs interconnected via an IP network illustrating the use of ENUM and a SAPC (scheme 1) for mobility services.
Figure 4:
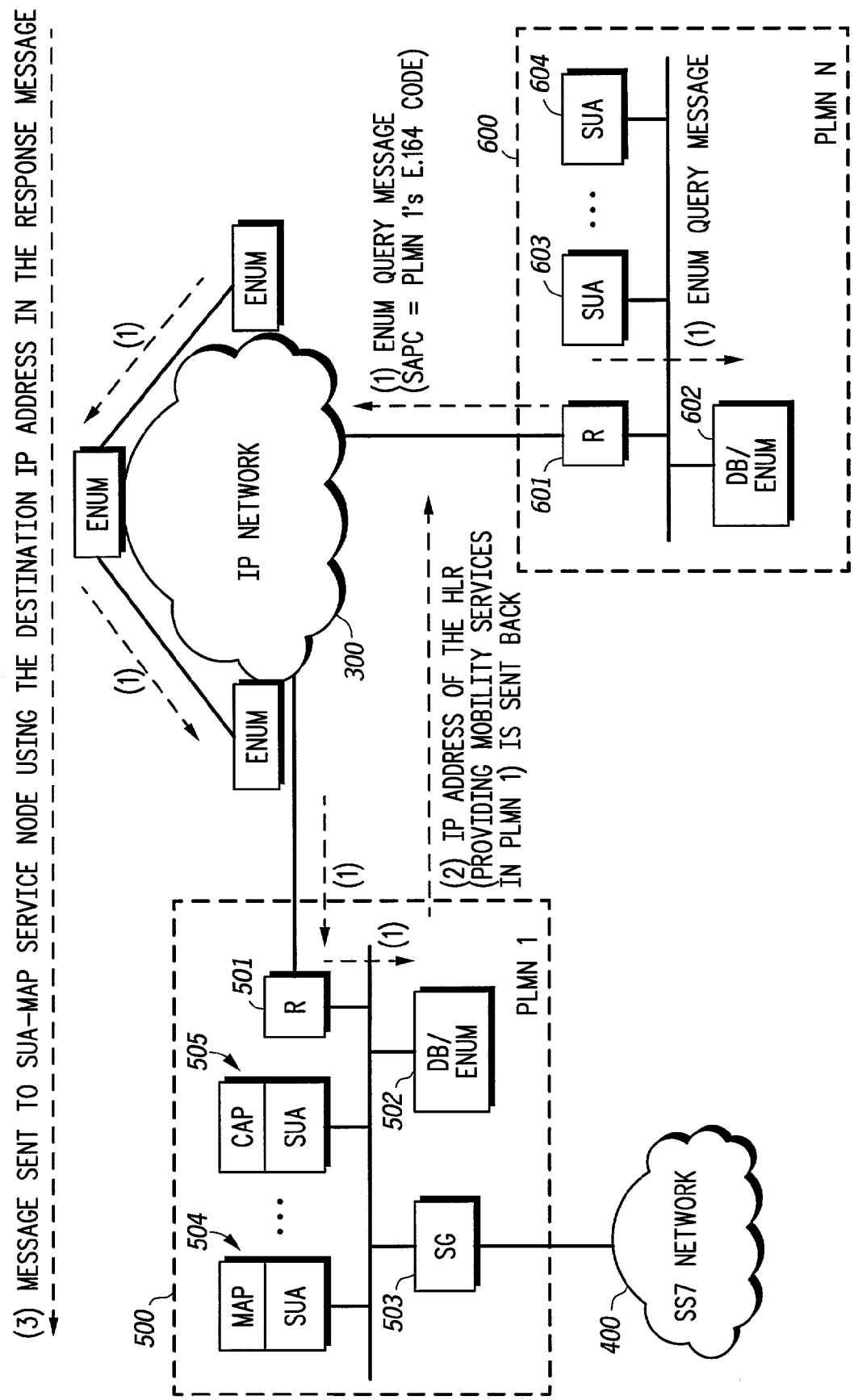
FIG. 4 is a block diagram depiction of PLMNs interconnected via an IP network illustrating the use of ENUM and a SAPC (scheme 2) for mobility services.
Figure 5:
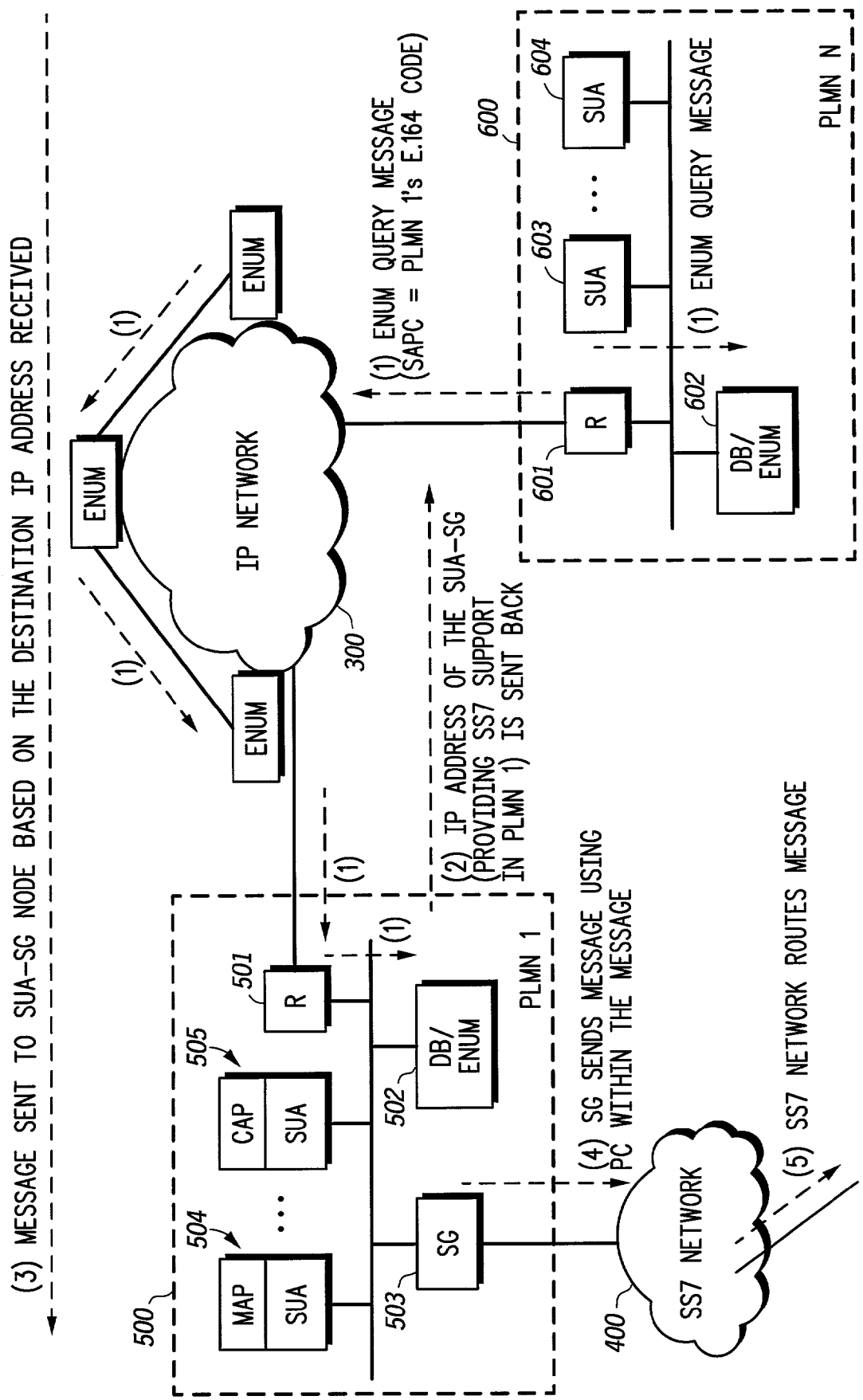
FIG. 5 is a block diagram depiction of PLMNs interconnected via an IP network illustrating service discovery using an SAPC (scheme 2) for a point code global title.
Figure 6:
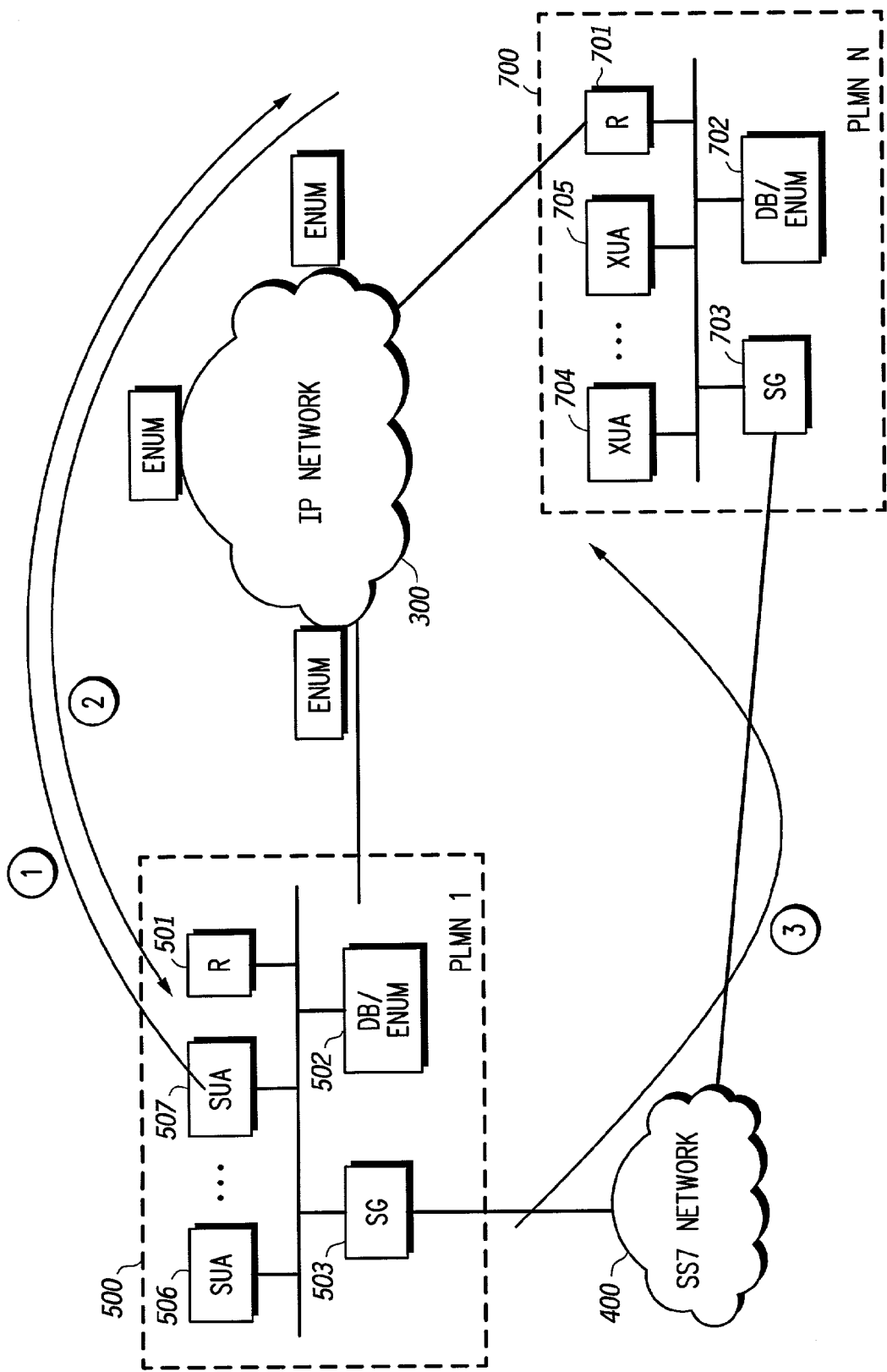
FIG. 6 is a block diagram depiction of PLMNs interconnected via an IP network illustrating the inter-working between two different SS7/IP protocols.

The present invention can be more fully understood with reference to FIGS. 1–6, wherein like numerals designate like components. As depicted in FIGS. 3–6, a preferred embodiment of the present invention is focused on IP communication (via IP network 300) between public land mobile networks (PLMNs) such as PLMNs 500, 600, and 700. A preferred PLMN comprises an IP router (e.g., 501, 601, or 701), an ENUM database (e.g., 502, 602, or 702), and service application nodes (e.g., 504, 505, 603, 604, 704, or 705). A preferred PLMN may also comprise a signaling gateway (e.g., 503 or 703) that interfaces to SS7 network 400. PLMNs, SS7 networks, and IP networks (including the ENUM functionality and the ENUM database hierarchy) are all well known in telecommunications as are their computer networking components and the software/firmware that enables the standards-based communication that they provide.

ENUM functionality is based on the IETF ENUM standard (RFC 2916) that uses domain name service (DNS) technology to map telephone numbers to Internet addresses. ENUM services are a core piece of Internet infrastructure that allow a communications application to efficiently "discover" IP-enabled communications services associated with a given telephone number. Discovery/retrieval of an IP address for a service application node can be based on any service URI (Universal Resource Identifier (RFC 1630)) specified in ENUM. In a preferred embodiment of the present invention, ENUM is used to identify/discover the IP address of a target service application node and/or identify/discover the service handling capability of a PLMN.

ENUM uses a Service Applications PLMN Code (SAPC) to discover IP addresses and/or PLMN service capabilities. By mapping the target MCC (Mobile Country Code) and MNC (Mobile Network Code), both retrieved from an IMSI, to an SAPC, the SAPC can be included in an ENUM query message to initiate the service/node discovery in another PLMN. Thus, the IMSI or an E.164 number for a subscriber can be used to discover the IP address and/or services of a target service application node. Intermediate ENUM servers will do the address mapping based on the domain names CC (Country Code) and NPA/NDC (National Planned Area/National Destination Code) only and need not carry any other E.164 related information at Tier 1 of the ENUM hierarchy. It should also be noted that the services entered in ENUM are under Tier2/Tier3 and are strictly under the control and administration of the operator in charge of that PLMN. DNS/ENUM will contain only E.164 numbers and the SAPC as an "exchange code". Only the operators having a roaming agreement need to populate their local ENUM with the SAPC code (s) of the PLMN of the operators with whom they have the agreement.

Two schemes are provided for SAPC assignment. Schemes 1 and 2 are illustrated by FIGS. 1 and 2, respectively. FIG. 1 shows an example of PLMNs providing a set of services/protocols where each service/protocol is represented by a unique SAPC. Services can be associated with a number of different subscriber ID schemes, such as: E.164 (CAP, MAP, SIP), E.212 (MAP), E.XXX (Dispatch/group calls), Point Codes (SS7 support service), etc. FIG. 2 shows an example of PLMNs providing a set of services/protocols where each PLMN is represented by a unique SAPC. Here, the SAPC is a unique E.164 number assigned to a PLMN providing a set of services.

In general, however, the SAPC concept applies to present mobility services as well as potential future services such as Instant Messaging and Dispatch that may not be based on or associated with an E.164 numbering scheme. In fact, services/protocols could be based on or associated with any numbering scheme. For example, services could be in support of the SS7 legacy network (e.g., data translation services to support the SS7 message routing functionality), Voice Dispatch service, and GT data types (E.212, E.214, E.164, point code as node address etc.). Also, a SAPC can be assigned to a specific service/protocol (for auto discovery of the services) or can be assigned to a GT-type specific node (SS7 equivalent of subscriber or node ID) that is capable of handling a specific data type translation. Thus, SAPCs identify a physical or a virtual node providing a specific service(s).

These service applications nodes can be defined by the service provider in any form or fashion, that is, a service application node's IP address can be provided in the local ENUM database depending on the type of services it provides or the GT types it is capable of handling. Service providers control what services they will provide to others by storing IP addresses and service indicators in their local ENUM DBs. Thus, as network operators reach roaming agreements with one another, for example, they can exchange the relevant SAPC's stored in each of their local ENUM databases for the services they will provide the other.

Once the target service application node's IP address is identified, a SCCP-User Adaptation Layer (SUA) node can transport signalling messages from SCCP users, such as Transaction Capabilities Application Part (TCAP), Radio Access Network Application Part (RANAP), and Radio Network Subsystem Application Part (RNSAP), to the target node over the Internet Protocol (IP) network using the Stream Control Transmission Protocol (SCTP). SUA nodes thus support the seamless interoperation between SCCP users in the SS7 and IP domains. Among the several adaptation protocols, SUA has significant advantages in an all IP environment as it eliminates the need for any additional SS7 protocols below the SCCP layer, including SCCP layer itself, thus removing the need for expensive and inflexible point codes addressing scheme.

Operation of a preferred embodiment in accordance with the present invention, occurs substantially as follows with reference to FIGS. 3–6. Four scenarios are described, each corresponding to one of the figures.

The first scenario (FIG. 3) describes the discovery and address retrieval of an end node (SUA as an example) residing in PLMN 1 (PLMN 500) by PLMN N (PLMN 600) via a DNS/ENUM query. This illustrates the use of ENUM for mobility services operation to discover the MAP URI/node IP address utilizing a scheme 1 SAPC. PLMN 1 and PLMN N are assumed to have a roaming agreement and are aware of the SAPC codes for each other's PLMN (DB/ENUM 502 and 602 each contain their respective SAPC codes). Note that these local ENUMs can contain either a virtual IP address or an IP address of the physical service application node providing mobility services (the HLR in this case). Service application nodes 504 and 505 employ SUA, although they could be based on any SS7/IP adaptation layer protocol. Also, it should be noted that generally discovery/retrieval of IP addresses for a service application node can be based on any service URI specified in ENUM and that generally service discovery can be based on a standard DNS/ENUM query with order and preference.

In the first scenario, PLMN 600 receives an IMSI from a mobile subscriber requesting registration. PLMN 600 obtains the MCC and MNC from the IMSI and sends an ENUM query message (1) using the SAPC corresponding to mobility services. ENUM/DB 502 receives the message (1), based on the SAPC looks up the IP address corresponding to SUA-MAP node 504, and responds (IP message 2) with the IP address of SUA-MAP node 504. After receiving the response, PLMN 600 can send an SUA message (3) to PLMN 500 using node 504's IP address.

The second scenario (FIG. 4) also describes the discovery and address retrieval of an end node (SUA as an example) residing in PLMN 1 by PLMN N via a DNS/ENUM query. It illustrates the use of mobility services operation using ENUM to discover the MAP URI/node IP address utilizing a scheme 2 SAPC. In the second scenario, PLMN 600 receives an IMSI from a mobile subscriber requesting registration. PLMN 600 obtains the MCC and MNC from the IMSI and sends an ENUM query message (1) using the SAPC from DB/ENUM 602 that corresponds to the MCC and MNC (this is the unique E.164 (ISDN) number for PLMN 500). ENUM/DB 502 receives the message (1), looks up the IP address corresponding to SUA-MAP node 504, and responds (IP message 2) with the IP address of SUA-MAP node 504. After receiving the response, PLMN 600 can send an SUA message (3) to PLMN 500 using node 504's IP address.

The third scenario (FIG. 5) illustrates service discovery with point code as the global title using a scheme 2 SAPC. It's an example of an "SS7 support service" that provides an inter-working function for the legacy SS7 networks using a point codes based addressing scheme. To illustrate this, a small satellite PLMN N, which is not capable of providing legacy SS7 network support via an SG, could utilize this service via PLMN 1. Therefore, using the SAPC concept in the ENUM domain, a satellite PLMN could identify the IP address of a specific service application node in another PLMN to be used for sending the subsequent SS7 applications messages to the legacy SS7 network.

In the third scenario, PLMN 600 receives an IMSI from a mobile subscriber requesting registration. PLMN 600 determines that the subscriber belongs to a PLMN with legacy SS7 support only. PLMN 600 obtains the MCC and MNC from the IMSI and sends an ENUM query message (1) using the SAPC from DB/ENUM 602 that corresponds to the MCC and MNC (this is the unique E.164 (ISDN) number for PLMN 500). ENUM/DB 502 receives the message (1), looks up the IP address corresponding to SUA-SG node 503, and responds (IP message 2) with the IP address of SUA-SG node 503. After receiving the response, PLMN 600 can send an SUA message (3) to PLMN 500 using node 503's IP address. Based on the point code within the SUA message (3), SUA-SG node 503 generates an SS7 message (4), and sends it via SS7 network 400. SS7 network 400 then routes the SS7 message (5) to the appropriate PLMN.

The fourth scenario (FIG. 6) describes how this invention can be used for inter-working between any two SS7/IP adaptation (XUA) protocols using scheme 2. This shows how the SAPC concept provides a graceful migration path for an operator, providing backward compatibility and inter-working with various SS7/IP protocols.

In the fourth scenario, SUA node 507 in PLMN 500 (SUA network) sends an ENUM query message (1) that is routed based on its SAPC to PLMN 700. Local DB/ENUM 702 in PLMN 700 (M3UA/XUA network) sends query response message (2) that includes XUA node 704's IP address and protocol ID as M3UA. SUA node 507 sends message (3) to SG 503, which routes the message to SS7 network 400. SS7 network 400 routes the message to SG 703, which performs a protocol conversion and routes the message to XUA node 704.

While the present invention has been particularly shown and described with reference to particular embodiments thereof, it will be understood by those skilled in the art that various changes in form and details may be made therein without departing from the spirit and scope of the present invention.

What is claimed is:

1. A method for a telecommunications network to communicate using an Internet protocol (IP) comprising the steps of:
    sending an IP query message to query for information associated with a service provided by a target telecommunications network, wherein the IP query message comprises a telephone number associated with the service provided by the target telecommunications network;
    receiving in response to the IP query message an IP address associated with the service;
    receiving, in response to the IP query message, the service provided by the target telecommunications network and
    sending an IP message to the target telecommunications network using the IP address associated with the service, wherein the service comprises at least one service selected from the group consisting of an adaptation protocol, SIP (session initiation protocol), MAP (Mobile Applications Part), CAP (CAMEL Applications Part), dispatch, point code, E.212, E.164, and E124.

2. A method for a telecommunications network to communicate using an Internet protocol (IP) comprising the steps of:
    sending an IP query message to query for information associated with a target telecommunications network, wherein the IP query message comprises a telephone number associated with the target telecommunications network;
    sending an IP address associated with the target telecommunications network;
    receiving in response to the IP query message the IP address associated with the target telecommunications network and a protocol associated with the target telecommunications network;
    determining based on the protocol that a protocol incapability exists; and
    sending an SS7 message to the target telecommunications network rather than an IP message.

3. The method of claim 2 wherein the IP query message comprises an IP ENUM/DNS (Domain name service) query message.

4. The method of claim 1 wherein the telephone number comprises an E.164 number used as a Service Applications PLMN Code (SAPC).

5. The method of claim 1 wherein the protocol associated with the target telecommunications network comprises an adaptation protocol.

6. A method for a telecommunications network to communicate using an Internet protocol (IP) comprising the steps of:
    sending an IP query message to query for information associated with a target telecommunications network, wherein the IP query message comprises a telephone number associated with the target telecommunications network;
    receiving, in response to the IP query message, an IP address associated with the target telecommunications network and at least one service provided by the target telecommunications network, wherein the at least one service comprises at least one service selected from the group consisting of an adaptation protocol, SIP (session initiation protocol), MAP (Mobile Applications Part), CAP (CAMEL Applications Part), dispatch, point code, E.212, E.164, and E.124; and
    sending an IP message to the target telecommunications network using the IP address associated with the target telecommunications network.

* * * * *